United States Patent [19]

Bollinger et al.

[11] 4,347,075
[45] Aug. 31, 1982

[54] METHOD FOR USING NICOTINIC ACID DERIVATIVES AS PLANT GROWTH REGULANTS

[75] Inventors: Frederic G. Bollinger; John J. D'Amico, both of St. Louis; Dale J. Hansen, St. Charles, all of Mo.

[73] Assignee: Monsanto Company, St. Louis, Mo.

[21] Appl. No.: 198,327

[22] Filed: Oct. 20, 1980

Related U.S. Application Data

[60] Division of Ser. No. 932,736, Aug. 9, 1978, Pat. No. 4,261,730, which is a continuation-in-part of Ser. No. 753,260, Dec. 22, 1976, abandoned.

[51] Int. Cl.$^3$ .............................................. A01N 43/40
[52] U.S. Cl. ......................................... 71/94; 546/263; 546/261; 546/322
[58] Field of Search .................. 546/261, 263, 322; 71/94

[56] References Cited

U.S. PATENT DOCUMENTS

| | | | |
|---|---|---|---|
| 3,119,831 | 1/1964 | Homer | 71/94 |
| 3,246,975 | 4/1966 | Hopkins et al. | 71/94 |
| 3,296,304 | 1/1967 | Tilley et al. | 71/94 |
| 3,330,641 | 7/1967 | Woods et al. | 71/94 |
| 3,376,307 | 4/1968 | Hyden et al. | 71/94 |
| 3,389,986 | 6/1968 | DiBella | 71/94 |
| 3,489,761 | 1/1970 | Kauer | 71/94 |
| 3,658,892 | 4/1972 | Martin et al. | 260/518 |
| 3,776,955 | 12/1973 | Zielinski | 71/94 |
| 4,086,078 | 4/1978 | Bollinger et al. | 71/94 |

FOREIGN PATENT DOCUMENTS

| | | | |
|---|---|---|---|
| 929965 | 1/1948 | France | |
| 1327227 | 8/1973 | United Kingdom | 546/309 |

OTHER PUBLICATIONS

Cooper et al., J. Chem. Soc. C, 1971, pp. 3257–3260.
Schmidt et al., Chem. Abst., 1956, vol. 50, No. 3376.
Pagani et al., Chem. Abst., 1968, vol. 69, No. 43588q.
Hoffman et al., Science 1949, vol. 109, p. 588.
Teubner, et al., Science 1955, vol. 122, pp. 74–75.

*Primary Examiner*—Henry R. Jiles
*Assistant Examiner*—Natalia Harkaway
*Attorney, Agent, or Firm*—Patricia A. Coburn; Howard C. Stanley

[57] ABSTRACT

Aromatic acids having the following formula

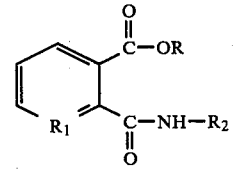

have been found to be effective plant growth regulants especially for the treatment of corn plants.

2 Claims, No Drawings

METHOD FOR USING NICOTINIC ACID DERIVATIVES AS PLANT GROWTH REGULANTS

This application is a divisional of Ser. No. 932,736 filed Aug. 9, 1978, now U.S. Pat. No. 4,261,730 which in turn is a Continuation-In-Part of Ser. No. 753,260, filed Dec. 22, 1976, now abandoned.

This invention relates to novel phthalamic acids and nicotinic acids and the salts thereof. Said compounds are useful as the active ingredient in plant growth regulating compositions. More particularly, the invention relates to the use of novel compounds having the formula

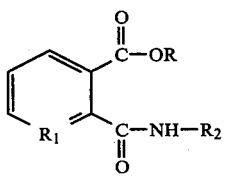

wherein R is hydrogen or lower alkyl; $R_1$ is carbon or nitrogen; $R_2$ is pyridyl, substituted pyridyl or when $R_1$ is nitrogen, $R_2$ may be substituted phenyl; and agriculturally acceptable salts thereof.

The term "substituted pyridyl" as used herein is understood to mean those radicals having the formulae

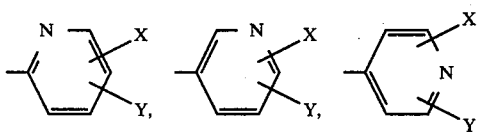

wherein X is selected from the group consisting of hydrogen, halogen, $CF_3$, lower alkyl and lower alkoxy; Y is selected from the group consisting of halogen, $CF_3$, lower alkyl and lower alkoxy; provided that neither X nor Y may be chlorine in the 4 position when the nitrogen atom is in the 3 position.

The term "substituted phenyl" as used herein is understood to mean those radicals having the formula

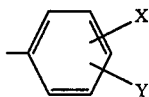

wherein X and Y are defined as above.

As used herein, the term "agriculturally acceptable salts" is understood to mean those salts formed from bases commonly used to form the salt of the free acid including, but not limited to, alkali metal, substituted amine and ammonium. For example, the salts may be formed from sodium, lithium, calcium, potassium, ammonia and various heterocyclic amines, such as, 2-amino-5-chloropyridine, 3-azabicyclo[3.2.2]nonane, cis- and trans-2,6-dimethylmorpholine, heptamethyleneimine, N-methylpiperazine, morpholine, hexamethyleneimine, pyrrolidine, piperidine, as well as other substituted amines such as cyclohexylamine, triethylamine, isopropylamine, diisopropylamine, dodecylamine, methylamine, N-methylcyclohexylamine, N-t-butyl-(2-cyanoethyl)amine, N-isopropylcyclohexylamine, N-ethyl-(2-cyanoethyl)amine, N-methyl-(2-cyanoethyl)amine, N-t-amylamine, N-allylcyclohexylamine, piperazine and 3-methoxypropylamine.

The terms "lower alkyl" and "lower alkoxy" are understood to include those alkyl and alkoxy radicals having from one to four carbon atoms inclusive.

The term "halogen" is understood to include chlorine, fluorine, bromine and iodine.

The phthalamic acids may be prepared by adding a stoichiometric equivalent of the appropriate aminopyridine to a slurry containing phthalic anhydride and chloroform. After stirring at room temperature, the precipitate may be filtered and air-dried. To illustrate the preparation of the novel phthalamic acids, the following examples are presented.

EXAMPLE 1

To a stirred slurry containing 0.1 moles of phthalic anhydride and 100 ml. of chloroform, 0.1 moles of 3-amino-2-chloropyridine was added in one portion. The reaction mixture was stirred for 24 hours. The precipitate was filtered, air-dried and identified as N-(2-chloro-3-pyridyl)phthalamic acid having a melting point of 203° C. (% yield=87).

Anal. Calc'd: Cl, 12.81; N, 10.12. Found: Cl, 12.94; N, 10.37.

In accordance with the procedure of Example 1, the following compounds have been prepared.

TABLE I

| Example | Compound | Analysis Calculated | Found |
|---|---|---|---|
| 2 | N-(6-methoxy-3-pyridyl)-phthalamic acid | C, 61.80; H, 4.44; N, 10.30 | C, 61.94; H, 4.42; N, 10.26 |
| 3 | N-(5-bromo-2-pyridyl)-phthalamic acid | N, 8.72; Br, 24.88 | N, 8.69; Br, 24.75 |
| 4 | N-(4,6-dimethyl-2-pyridyl)-phthalamic acid | C, 66.65; H, 5.22; N, 10.36 | C, 66.53; H, 5.28; N, 10.35 |

Alkali metal salts may be prepared by reaction of the free acid with the hydroxide of the alkali metal. Illustrative of such a reaction are Examples 5, 6, 7 and 8.

EXAMPLE 5

A mixture containing 27.7 g (0.1 mole) of N-(2-chloro-3-pyridyl)phthalamic acid, 500 ml. of water and 0.1 moles of sodium hydroxide is stirred at 25°-30° C. for about 15 minutes. The water is removed in vacuo at a maximum temperature of 98°-99° C. at 1-2 mm. Data is summarized in Table II.

EXAMPLE 6

The procedure of Example 5 is repeated using 0.1 mole of potassium hydroxide in lieu of sodium hydroxide.

EXAMPLE 7

The procedure of Example 5 is repeated using 0.1 mole of lithium hydroxide in lieu of sodium hydroxide.

TABLE II

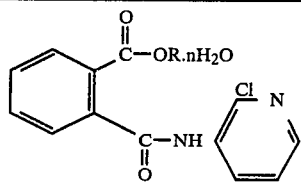

| Compound of Ex. No. | R | n | M.P. °C. | | %C | %H | %Cl | %N | %O | %R |
|---|---|---|---|---|---|---|---|---|---|---|
| 5 | Na* | zero | 246–7 | Calc'd: | 52.28 | 2.70 | 11.87 | 9.38 | 16.07 | 7.70 |
| | | | | Found: | 51.90 | 2.81 | 11.93 | 9.15 | 16.14 | 8.08 |
| 6 | K* | ½ | 152–4 | Calc'd: | 48.22 | 2.80 | 10.95 | 8.65 | 17.29 | 12.08 |
| | | | | Found: | 47.97 | 2.69 | 11.11 | 8.59 | 17.31 | 11.97 |
| 7 | Li* | zero | 183–5 | Calc'd: | 55.25 | 2.85 | 12.54 | 9.91 | 16.98 | 2.46 |
| | | | | Found: | 55.12 | 2.88 | 12.49 | 9.77 | 16.74 | 2.62 |

*Theoretical yields were obtained.

EXAMPLE 8

The procedure of Example 5 is repeated utilizing 0.06 moles of $Ca(OH)_2$ in lieu of sodium hydroxide resulting in the calcium salt of N-(2-chloro-3-pyridyl)phthalamic acid, decomposing at 290° C.

Anal. Calc'd. for $C_{26}H_{16}Cl_2N_4O_6Ca \cdot H_2O$: C, 51.24; H, 2.98; Cl, 11.63; N, 9.19; O, 18.38. Found: C, 50.54; H, 2.72; Cl, 11.31; N, 8.96; O, 17.96.

Amine salts may be prepared by reaction of an excess of the appropriate amine with the free acid.

EXAMPLE 9

To a stirred slurry containing 27.7 g (0.1 mole) of N-(2-chloro-3-pyridyl)phthalamic acid in 650 ml. of ethyl ether, 0.11 moles of 2-amino-5-chloropyridine is added. The solid salt is collected by filtration and air-dried at 25°–30° C. Data is summarized in Table III, below.

Table III also includes data for salts prepared utilizing the procedure of Example 9 wherein the amount of excess amino may be slightly different. The amount of excess is noted in Table III.

TABLE III

| Compound of Ex. No. | R | % Excess | M.P. °C. | % Yield | | %C | %H | %Cl | %N |
|---|---|---|---|---|---|---|---|---|---|
| 9 | H₂N–(pyridyl-Cl) | 10 | 153–5 | 94 | Calc'd: | 53.35 | 3.48 | 17.50 | 13.83 |
| | | | | | Found: | 53.44 | 3.53 | 17.43 | 13.74 |
| 10 | HN(CH₂)₂(cyclohexyl) | 10 | 147–8 | 99 | Calc'd: | 62.76 | 6.02 | 8.82 | 10.46 |
| | | | | | Found: | 62.80 | 6.09 | 8.76 | 10.42 |
| 11 | HN(CH(CH₃)CH₂)₂O | 100 | 137–8 | 98 | Calc'd: | 58.24 | 5.66 | 9.05 | 10.72 |
| | | | | | Found: | 58.09 | 5.70 | 9.09 | 10.71 |
| 12 | $H_2NC_6H_{11}$ | 100 | 144–6 | 95 | Calc'd: | 60.39 | 6.40 | 9.38 | 11.12 |
| | | | | | Found: | 60.42 | 6.34 | 9.24 | 11.08 |
| 13 | HN(CH₂)₂(CH₂)₅ | 100 | 128–9 | 96 | Calc'd: | 61.61 | 6.20 | 9.09 | 10.78 |
| | | | | | Found: | 61.34 | 6.29 | 9.04 | 10.69 |

TABLE III-continued

[Reaction scheme: 2-(phthalamic acid)-N-(chloropyridyl) + R → corresponding salt with R]

| Compound of Ex. No. | R | % Excess | M.P. °C. | % Yield | | % C | % H | % Cl | % N |
|---|---|---|---|---|---|---|---|---|---|
| 14 | HN(CH$_2$CH$_2$)$_2$NCH$_3$ (N-methylpiperazine) | 10 | 142–3 | 99 | Calc'd:<br>Found: | 57.37<br>57.29 | 5.62<br>5.66 | 9.41<br>9.37 | 14.87<br>14.81 |
| 15 | HN(CH$_2$CH$_2$)$_2$O (morpholine) | 100 | 131–3 | 98 | Calc'd:<br>Found: | 56.13<br>56.18 | 4.99<br>5.03 | 9.75<br>9.72 | 11.55<br>11.49 |
| 16 | HN(CH$_2$)$_2$(CH$_2$)$_4$(CH$_2$) (bicyclic amine) | 100 | 120–2 | 81 | Calc'd:<br>Found: | 60.72<br>60.77 | 5.90<br>5.94 | 9.43<br>9.48 | 11.18<br>11.15 |
| 17 | HN (pyrrolidine) | 100 | 133–5 | 96 | Calc'd:<br>Found: | 58.71<br>58.72 | 5.22<br>5.24 | 10.19<br>10.16 | 12.08<br>12.02 |
| 18 | HN (piperidine) | 100 | 136–8 | 72 | Calc'd:<br>Found: | 59.75<br>59.79 | 5.57<br>5.59 | 9.80<br>9.84 | 11.61<br>11.58 |
| 19 | H$_2$NCH(CH$_3$)$_2$ | 100 | 134–5 | 95 | Calc'd:<br>Found: | 57.23<br>56.99 | 5.40<br>5.44 | 10.56<br>10.47 | 12.51<br>12.38 |
| 20 | HN(CH(CH$_3$)$_2$)$_2$ | 100 | 123–5 | 92 | Calc'd:<br>Found: | 60.39<br>60.23 | 6.40<br>6.46 | 9.38<br>9.34 | 11.12<br>11.06 |
| 21 | HNC$_6$H$_{11}$ / CH$_3$ | 100 | 139–41 | 99 | Calc'd:<br>Found: | 61.61<br>61.69 | 6.20<br>6.22 | 9.09<br>9.04 | 10.78<br>10.77 |
| 22 | HNC(CH$_3$)$_3$ / CH$_2$CH$_2$CN | 100 | 158–60 | 99 | Calc'd:<br>Found: | 59.48<br>59.61 | 5.99<br>5.77 | 8.78<br>8.90 | 13.87<br>13.86 |
| 23 | HNCH(CH$_3$)$_2$ / C$_6$H$_{11}$ | 100 | 156–8 | 90 | Calc'd:<br>Found: | 63.23<br>63.32 | 6.75<br>6.80 | 8.48<br>8.43 | 10.05<br>10.00 |
| 24 | HNC$_2$H$_5$ / CH$_2$CH$_2$CN | 100 | 146–8 | 99 | Calc'd:<br>Found: | 57.68<br>57.67 | 5.11<br>5.12 | 9.46<br>9.50 | 14.95<br>14.94 |
| 25 | HNCH$_3$ / CH$_2$CH$_2$CN | 100 | 140–2 | 99 | Calc'd:<br>Found: | 56.59<br>56.61 | 4.75<br>4.78 | 9.83<br>9.80 | 15.53<br>15.56 |
| 26 | HN(CH$_2$CH$_2$)$_2$NH (piperazine) | (a) | 194–6 | 99 | Calc'd:<br>Found: | 56.35<br>56.18 | 4.41<br>4.43 | 11.09<br>10.98 | 13.14<br>13.08 |
| 27 | H$_2$NC(CH$_3$)$_2$C$_2$H$_5$ | 20 | 142–4 | 88 | Calc'd:<br>Found: | 59.42<br>59.45 | 6.09<br>6.14 | 9.74<br>9.72 | 11.55<br>11.52 |
| 28 | HNCH$_2$CH=CH$_2$ / C$_6$H$_{11}$ | 100 | 115–7 | 94 | Calc'd:<br>Found: | 63.53<br>63.65 | 6.30<br>6.35 | 8.52<br>8.51 | 10.10<br>10.06 |
| 29 | H$_2$N(CH$_2$)$_3$OCH$_3$ | 100 | 127–9 | 98 | Calc'd: | 55.82 | 5.51 | 9.69 | 11.49 |

TABLE III-continued

[Reaction scheme: phthalamic acid with chloropyridine + R → salt product]

| Compound of Ex. No. | R | % Excess | M.P. °C. | % Yield | % C | % H | % Cl | % N |
|---|---|---|---|---|---|---|---|---|
| | | | | Found: | 55.83 | 5.54 | 9.64 | 11.49 |

(a) 0.1 mole N-(2-chloro-3-pyridyl)phthalamic acid and 0.06 mole of piperazine were employed.

EXAMPLE 30

To a stirred slurry containing 27.7 g (0.1 mole) of N-(2-chloro-3-pyridyl)phthalamic acid in 650 ml. of ethyl ether, 0.2 moles of methylamine is added by bubbling at 25°–30° C. for about 15 minutes. The reaction mixture is stirred for 24 hours at 25°–30° C. The methylamine salt of N-(2-chloro-3-pyridyl)phthalamic acid, m.p. 137°–9° C., was collected by filtration and air-dried at 25°–30° C. The yield was 98%.

Anal. Calc'd: C, 54.64; H, 4.59; Cl, 11.52; N, 13.65. Found: C, 54.51; H, 4.64; Cl, 11.40; N, 13.73.

EXAMPLE 31

The procedure of Example 30 is repeated utilizing ammonia in lieu of methylamine. The ammonium salt of N-(2-chloro-3-pyridyl)phthalamic acid, m.p. 173°–5° C., was obtained in 99% yield.

Anal. Calc'd: C, 53.16; H, 4.12; Cl, 12.07; N, 14.31. Found: C, 53.16; H, 4.15; Cl, 12.04; N, 14.30.

EXAMPLE 32

To a stirred slurry containing 27.7 g (0.1 mole) of N-(2-chloro-3-pyridyl)phthalamic acid in 650 ml. of ethyl ether, 0.11 moles of dodecylamine is added in one portion. The excess amine and ether are removed in vacuo at a maximum temperature of 45°–50° C. at 1–2 minutes. The dodecylamine salt of N-(2-chloro-3-pyridyl)phthalamic acid, m.p. 70°–2° C., was obtained in 99% yield.

Anal. Calc'd: C, 64.99; H, 7.85; N, 9.09. Found: C, 65.31; H, 8.21; N, 8.86.

EXAMPLE 33

The procedure of Example 32 is repeated utilizing 0.2 moles of triethylamine in lieu of 0.11 moles of dodecylamine. The triethylamine salt of N-(2-chloro-3-pyridyl)phthalamic acid is obtained as a viscous liquid in 99% yield.

Anal. Calc'd: Cl, 9.38; N, 11.12. Found: Cl, 9.22; N, 10.86.

EXAMPLE 34

To a stirred slurry containing 27.7 g (0.1 mole) of N-(5-chloro-2-pyridyl)phthalamic acid in 650 ml. of ethyl ether, 0.2 moles of pyrrolidine is added in one portion. The reaction mixture is stirred at 25°–30° C. for 24 hours. The pyrrolidine salt of N-(5-chloro-2-pyridyl)phthalamic acid, m.p. 147°–9° C., was collected by filtration and air-dried at 25°–30° C. The yield was 92%.

Anal. Calc'd: C, 58.71; H, 5.22; Cl, 10.19; N, 12.08. Found: C, 58.72; H, 5.27; Cl, 10.10; N, 12.09.

Table IV summarizes data obtained when the process of Example 34 is repeated utilizing different amines to form different salts.

TABLE IV

[Reaction scheme: N-(5-chloro-2-pyridyl)phthalamic acid + R → salt]

| Compound of Ex. No. | R | % Excess | M.P. °C. | % Yield | | % C | % H | % Cl | % N |
|---|---|---|---|---|---|---|---|---|---|
| 35 | HN(CH₂)₂(CH₂)₄(CH₂) (piperidine) | 100 | 147–9 | 93 | Calc'd: | 60.72 | 5.90 | 9.43 | 11.18 |
| | | | | | Found: | 60.55 | 5.97 | 9.35 | 11.14 |
| 36 | HN–O (morpholine) | 100 | 141–3 | 88 | Calc'd: | 56.13 | 4.99 | 9.75 | 11.55 |
| | | | | | Found: | 56.17 | 5.02 | 9.83 | 11.53 |
| 37 | HN(CH₂)(CH₂) (cyclic amine) | 10 | 152–4(a) | 83 | Calc'd: | 62.76 | 6.02 | 8.82 | 10.46 |
| | | | | | Found: | 63.01 | 5.97 | 8.91 | 10.35 |

TABLE IV-continued

Reaction scheme: 2-(C(=O)OH)-C$_6$H$_4$-C(=O)-NH-(5-chloropyridin-2-yl) + R → 2-(C(=O)OHR)-C$_6$H$_4$-C(=O)-NH-(5-chloropyridin-2-yl)

| Compound of Ex. No. | R | % Excess | M.P. °C. | % Yield | | % C | % H | % Cl | % N |
|---|---|---|---|---|---|---|---|---|---|
| 38 | HN(CH$_2$)(CH$_2$)(CH$_2$)$_5$ (hexahydroazepine) | 10 | 153-5$^{(a)}$ | 90 | Calc'd: | 61.61 | 6.20 | 9.09 | 10.78 |
|  |  |  |  |  | Found: | 61.74 | 6.18 | 9.19 | 10.75 |
| 39 | H$_2$NC$_6$H$_{11}$ | 100 | 168-70 | 95 | Calc'd: | 60.39 | 6.40 | 9.38 | 11.12 |
|  |  |  |  |  | Found: | 60.78 | 6.14 | 9.58 | 10.97 |
| 40 | H$_2$N(CH$_2$)$_3$OCH$_3$ | 100 | 151-3 | 93 | Calc'd: | 55.82 | 5.51 | 9.69 | 11.49 |
|  |  |  |  |  | Found: | 55.79 | 5.53 | 9.65 | 11.46 |
| 41 | HNC$_6$H$_{11}$ / CH$_3$ | 100 | 151-3 | 88 | Calc'd: | 61.61 | 6.20 | 9.09 | 10.78 |
|  |  |  |  |  | Found: | 61.45 | 6.28 | 9.03 | 10.78 |

$^{(a)}$Recrystallization from toluene.

EXAMPLE 42

To a stirred slurry containing 27.7 g (0.1 mole) of N-(5-chloro-2-pyridyl)phthalamic acid in 650 ml. of ethyl ether, 0.2 moles of ammonium gas is bubbled at 25°-30° C. over a 15-minute period. The reaction mixture is stirred for 24 hours at 25°-30° C. The ammonium salt of N-(5-chloro-2-pyridyl)phthalamic acid, m.p. 155°-6° C., is collected by filtration and air-dired at 25°-30° C.

Anal. Calc'd: C, 53.16; H, 4.12; Cl, 12.07; N, 14.31.

EXAMPLE 43

To a stirred slurry of 0.1 mole of N-(2-chloro-3-pyridyl)phthalamic acid and 500 ml. of ethyl ether, 0.11 mole of isopropylamine, to form the isopropylamine salt, was added in one portion. After stirring at 25°-30° C. for 24 hours, a solid was collected by filtration and air-dried. The product, m.p. 147°-148° C., was obtained in 100% yield.

Anal. Calc'd: C, 57.23; H, 5.40; Cl, 10.56; N, 12.61. Found: C, 57.68; H, 5.45; Cl, 10.71; N, 12.59.

EXAMPLE 44

The procedure of Example 43 was followed to prepare the isopropylamine salt of N-(5-bromo-2-pyridyl)phthalamic acid, m.p. 145°-146° C., in 87% yield.

Anal. Calc'd: C, 50.54; H, 4.77; N, 11.05. Found: C, 50.42; H, 4.73; N, 10.99.

Esters may be prepared as follows.

EXAMPLE 45

To a stirred slurry containing 27.7 g (0.1 mole) of N-(2-chloro-3-pyridyl)phthalamic acid and 300 ml. of methyl alcohol, 71 g (0.5 mole) of boron trifluoride etherate [(C$_2$H$_5$)$_2$O.BF$_3$] is added in one portion. An exothermic reaction set in causing a temperature rise from 21° to 33° C. The stirred mixture is heated at reflux for 24 hours. After cooling to −10° C., 1000 ml. of a 10% aqueous sodium bicarbonate solution is added slowly at −10° to 0° C. After stirring at 0° to 10° C. for 30 minutes, the solid is collected by filtration, washed with water until neutral and air-dried at 25°-30° C. The product, which is the methyl ester of N-(2-chloro-3-pyridyl)phthalamic acid, m.p. 110°-112° C., is obtained in 76% yield. After two recrystallizations from heptane/isopropyl alcohol, it melted at 122°-124° C.

Anal. Calc'd. for C$_{14}$H$_{11}$ClN$_2$O$_3$: C, 57.84; H, 3.81; Cl, 12.20; N, 9.64. Found: C, 57.88; H, 3.57; Cl, 12.45; N, 9.41.

The nicotinic acids of the present invention may be prepared by adding 0.1 mole of the appropriate substituted aniline or aminochloropyridine to a slurry of 0.1 mole of 2,3-pyridine dicarboxylic acid anhydride and 100 ml. of chloroform. After stirring at 25°-30° C. for 24 hours, the solids are collected by filtration and air-dried at 25°-30° C. The compounds of Examples 46-53, summarized by Table V below, were prepared in accordance with the above procedure.

TABLE V

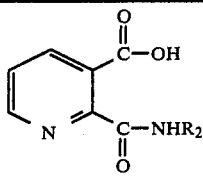

| Compound of Ex. No. | R₂ | M.P. °C. | % Yield | Percent C Calc'd. | Percent C Found | Percent H Calc'd. | Percent H Found | Percent N Calc'd. | Percent N Found |
|---|---|---|---|---|---|---|---|---|---|
| 46 | phenyl-2,?-(OCH₃)₂ | 178–9(a) | 95 | 59.60 | 59.62 | 4.67 | 4.69 | 9.27 | 9.31 |
| 47 | phenyl-CF₃ | 111–2(b) | 90 | 54.20 | 54.37 | 2.92 | 3.07 | — | — |
| 48 | phenyl-Cl,CF₃ | 138–9(c) | 73 | 48.79 | 48.69 | 2.34 | 2.31 | 8.31 | 8.18 |
| 49 | phenyl-(CF₃)₂ | 174–5(b) | 47.63 | 47.89 | 2.13 | 2.10 | 7.41 | 7.30 | | |
| 50 | pyridyl-Cl | 150–1(a) | 94 | 51.91 | 51.47 | 2.90 | 3.02 | 15.13 | 15.47 |
| 51 | phenyl-CF₃,Cl | 184–5(d) | 96 | 48.79 | 48.68 | 2.34 | 2.25 | 8.13 | 8.04 |
| 52 | phenyl-CF₃ | 163–4(d) | 82 | 54.20 | 54.08 | 2.92 | 2.88 | 9.03 | 9.18 |
| 53 | phenyl-CF₃ | 182–3(c) | 95 | 54.20 | 54.07 | 2.92 | 2.89 | — | — |

(a)Recrystallization from methyl alcohol.
(b)Recrystallization from heptane/isopropyl alcohol.
(c)Recrystallization from NaOH/HCl.
(d)Recrystallization from isopropyl alcohol.

The compounds represented by Formula I above have been found to be effective in altering the development of both the male (tassel) and female (ear) reproductive components of corn plants. As used herein, the alteration of the "development of the reproductive component" of the corn plant is understood to mean the modification of the normal sequential development of said component to maturity. Such modifications are most readily observed as inhibition of tassel growth, inhibition of lateral tassel branches, alteration in ear numbers, shape, position, kernel numbers, speed of silking, etc.

The invention contemplates the alteration of the development of the reproductive components of healthy corn plants by applying an effective, non-lethal amount of the acids of Formula I to said corn plant before or during the early stages of the development of said reproductive component referred to herein as reproductive differentiation. As a result of such application, tassel size can be reduced or eliminated, thus reducing or eliminating the labor required by hybrid seed corn producers to manually detassel said corn plants. Additionally, the amount of speed per unit area of land can, in some instances, be increased by appling an effective amount of the active ingredient before or during the early stages of the development of said ear. Positive results are dependent upon plant variety, rate of application and time of application and have been found with the A-619 variety at less than two pounds per acre when applied within 12 days after the seedling emerged.

As used herein, the term "active ingredient" refers to the acids of Formula I.

In accordance with the novel aspects of the present invention, many of the compounds of the invention were tested in accordance with the following procedure.

EXAMPLE A

A-619 variety corn plants were grown and thinned to obtain a uniform population. All weak or late plants were removed before chemical application. The active ingredient was formulated by adding 50 or 100 mg. of the active ingredient to 7.5 ml. of acetone and 7.5 ml. of water. 0.25% Tween 20 was added as a surfactant. Utilizing a Devilbiss #152 sprayer, the corn plants were sprayed during the early stages of reproductive differentiation at a rate of 10 mg. per plant or 20 mg. per plant.

Results were analyzed by comparing the treated plants to control plants which were not chemically treated. Chemicals were considered to be active in altering the reproductive development of the corn plant if treatment resulted in an inhibition of at least 25 percent of the lateral tassel formation when compared to the control plants.

In accordance with the above procedure, compounds 1, 2, 5 and 46–48 were found to be effective in inhibiting from 50 to 74 percent of the lateral tassel development. Compounds 3, 43, 44 and 49–53 were found to be effective in inhibiting from 25 to 49 percent of the lateral tassel development. In addition, male flowering was inhibited as illustrated in Table VI.

TABLE VI

| Compound | cm. of Flowers |
|---|---|
| Control | 224 |
| 1 | 67 |
| 3 | 132 |
| 4 | 75 |

EXAMPLE B

In another test, N-(2-chloro-3-pyridyl)phthalamic acid was applied to corn plants as a formulation described above. Responses noted included alteration of ear height, increased speed of silking and partial sterility. Table VII illustrates the responses noted.

TABLE VII

| Rate of Treatment kilos/hectare | | | Ear Height (cm) | Percent of Male Sterility |
|---|---|---|---|---|
| Day 9[a] | Day 12[a] | Day 15[a] | | |
| 0 | 0 | 0 | 48 | 0 |
| 1.12 | 1.12 | 0 | 73 | 80 |
| 1.12 | 0 | 1.12 | 54 | 88 |
| 1.12 | 0.56 | 0 | 57 | 75 |
| 1.12 | 0 | 0.56 | 52 | 89 |
| 0.56 | 1.12 | 0 | 60 | 68 |
| 0.56 | 0 | 1.12 | 48 | 95 |
| 0.56 | 0.56 | 0 | 55 | 74 |
| 0.56 | 0 | 0.56 | 48 | 88 |

[a]from seedling emergence.

As exemplified above, the invention contemplates the application of the phthalamic acids before or during the early stages of the reproductive differentiation. Reproductive differentiation occurs at different times depending upon the variety of corn plant as well as environmental factors. For example, male reproductive differentiation of Gaspé corn begins during kernel formation while reproduction differentiation of A-619 corn begins within the first 8 to 12 days after seedling emergence. The determination of when reproductive differentiation occurs is within the skill of the art. By way of example and for purposes of illustration only, applications for most varieties used in the Midwest of the United States ranging from 3 to 25 days after seedling emergence are desirable. Varieties used in foreign countries may require applications ranging from 1 to 40 days from seedling emergence.

In the practice of the invention, the active ingredient can be used alone or in combination with a material referred to in the art as an adjuvant in either liquid or solid form. To prepare plant growth regulating compositions, the active ingredient is admixed with an adjuvant including diluents, extenders, carriers and conditioning agents to provide compositions in the form of finely-divided particulate solids, granules, pellets, wettable powders, dusts, solutions and aqueous dispersions or emulsions. Thus, the active ingredient can be used with an adjuvant such as a finely-divided particulate solid, a solvent liquid of organic origin, water, a wetting agent, dispersing agent or emulsifying agent or any suitable combination of these.

Illustrative finely-divided solid carriers and extenders which are useful in plant growth regulating compositions of this invention include the talcs, clays, pumice, silica, diatomaceous earth, quartz, Fullers earth, sulfur, powdered cork, powdered wood, walnut flour, chalk, tobacco dust, charcoal and the like. Typical liquid diluents include Stoddard solvent, acetone, alcohols, glycols, ethyl acetate, benzene and the like. The plant growth regulating compositions of this invention, particularly liquids and wettable powders, usually contain one or more surface-active agents in amounts sufficient to render a given composition readily dispersible in water or in oil. The term "surface-active agent" is understood to include wetting agents, dispersing agents, suspending agents and emulsifying agents. Such surface-active agents are well known and reference is made to U.S. Pat. No. 2,547,724, Columns 3 and 4, for detailed examples of the same.

Generally, the active ingredients are applied in the form of a composition containing one or more adjuvants which aid in the application of a uniform distribution of the active ingredient. The application of liquid and particulate solid compositions of the active ingredient can be carried out by conventional techniques utilizing, for example, spreaders, power dusters, boom and hand sprayers and spray dusters. The composition can also be applied from airplanes as a dust or spray.

Compositions of this invention generally contain from about 1 to 99 parts active ingredient, about 1 to 50 parts surface-active agent and about 4 to 94 parts solvents, all parts being by weight based on the total weight of the composition.

In selecting the appropriate rate of application of the active ingredient, it will be recognized that precise rates will also be dependent upon the mode of application, plant variety, soil conditions and various other factors known to those skilled in the art. While a rate of about 0.056 to 5.6 kilos per hectare is preferred, higher rates of up to 56 kilos per hectare may be used, depending upon the factors noted above.

This invention, however, does not contemplate the use of phytotoxic rates which exert a herbicidal effect. In addition, it will be recognized that single or multiple applications may be used to exert the desired response.

Although this invention has been described with respect to specific modifications, the details thereof are not to be construed as limitations, for it will be apparent that various equivalents, changes and modifications may be resorted to without departing from the spirit and scope thereof and it is understood that such equivalent embodiments are intended to be included herein.

The embodiments of the invention in which an exclusive property or privilege is claimed are defined as follows:

1. A method for altering the development of the reproductive components of a corn plant which comprises applying to said corn plant an effective, non-lethal amount of a compound of the formula

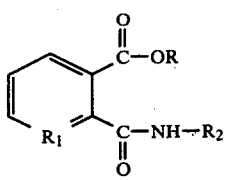

wherein R is hydrogen or lower alkyl; $R_1$ is nitrogen; $R_2$ is

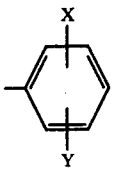

pyridyl,

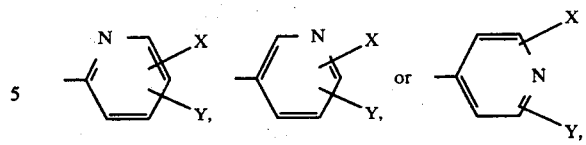

wherein X is hydrogen, halogen, $CF_3$, lower alkyl or lower alkoxy; Y is halogen, $CF_3$, lower alkyl or lower alkoxy; provided that neither X nor Y may be chlorine in the 4 position when the nitrogen atom is in the 3 position; and agriculturally acceptable salts thereof.

2. A method according to claim 1 wherein said compound has the formula

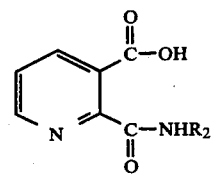

wherein $R_2$ is pyridyl, substituted pyridyl or substituted phenyl.

* * * * *